United States Patent
Son et al.

(10) Patent No.: US 11,021,418 B2
(45) Date of Patent: Jun. 1, 2021

(54) METHOD OF OLEFIN OLIGOMERIZATION

(71) Applicants: SK Innovation Co., Ltd., Seoul (KR); SK Global Chemical Co., Ltd., Seoul (KR)

(72) Inventors: Sungreal Son, Daejeon (KR); Hyoseung Park, Daejeon (KR); Inhyoup Song, Daejeon (KR); So Hee Sim, Daejeon (KR); Chansaem Park, Daejeon (KR); Woosung Jung, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 16/649,900

(22) PCT Filed: Jul. 18, 2018

(86) PCT No.: PCT/KR2018/008102
§ 371 (c)(1),
(2) Date: Mar. 23, 2020

(87) PCT Pub. No.: WO2019/066224
PCT Pub. Date: Apr. 4, 2019

(65) Prior Publication Data
US 2020/0262767 A1 Aug. 20, 2020

(30) Foreign Application Priority Data
Sep. 29, 2017 (KR) .................. 10-2017-0127147

(51) Int. Cl.
C07C 2/32 (2006.01)
C07C 7/04 (2006.01)
(Continued)

(52) U.S. Cl.
CPC .................. *C07C 2/32* (2013.01); *C07C 7/04* (2013.01); *C07C 7/20* (2013.01); *C07C 11/02* (2013.01); *C07C 2531/22* (2013.01)

(58) Field of Classification Search
CPC ............................ C07C 2531/22; Y02P 20/52
See application file for complete search history.

(56) References Cited

U.S. PATENT DOCUMENTS 6,147,133 A 11/2000 Sulzbach et al.
6,380,451 B1 * 4/2002 Kreischer .............. B01J 19/002
134/22.14
(Continued)

FOREIGN PATENT DOCUMENTS

KR 20000015923 A 3/2000
KR 1020090031575 A 3/2009
(Continued)

*Primary Examiner* — Ali Z Fadhel
(74) *Attorney, Agent, or Firm* — The Webb Law Firm

(57) ABSTRACT

The present invention relates to a method for olefin oligomerization, and can provide a method for olefin oligomerization. The method includes the steps of: introducing an oligomerization transition metal catalyst, olefin monomers, and a solvent into a reactor and performing an olefin oligomerization reaction to produce an oligomer; introducing a catalyst deactivator to a reaction product of the oligomerization reaction to deactivate the catalyst, with the catalyst deactivator including at least one functional group containing at least one selected from the group including oxygen, phosphor, nitrogen, and sulfur and having a number average molecular weight of 400 or more; separating the oligomer through distillation in a distiller; and separating the catalyst deactivator through the bottom end of the distiller.

10 Claims, 1 Drawing Sheet

(51) Int. Cl.
*C07C 7/20* (2006.01)
*C07C 11/02* (2006.01)

(56) References Cited

U.S. PATENT DOCUMENTS

| | | |
|---|---|---|
| 7,906,614 B2 | 3/2011 | Vanspeybroeck |
| 8,809,613 B2 | 8/2014 | Fritz et al. |
| 9,375,708 B2 | 6/2016 | Kreischer et al. |
| 9,593,055 B2 | 3/2017 | Aliyev et al. |
| 10,471,416 B2 | 11/2019 | Im et al. |
| 2004/0236163 A1* | 11/2004 | Ewert ................. B01J 31/4015 585/1 |
| 2010/0113851 A1* | 5/2010 | Kreischer ............ B01J 31/0239 585/511 |
| 2012/0016097 A1* | 1/2012 | Weber ....................... C07C 2/30 526/348 |
| 2013/0228723 A1* | 9/2013 | Yang ......................... C08F 2/42 252/402 |
| 2013/0303817 A1* | 11/2013 | Shaik ....................... C07C 2/30 585/504 |
| 2017/0305811 A1* | 10/2017 | Shin ....................... B01J 31/188 |
| 2018/0354870 A1* | 12/2018 | Wei ........................... B01J 21/08 |
| 2019/0308178 A1 | 10/2019 | Lee et al. |

FOREIGN PATENT DOCUMENTS

| | | |
|---|---|---|
| KR | 1020100113534 A | 10/2010 |
| KR | 1020110090900 A | 8/2011 |
| KR | 1020120050963 A | 5/2012 |
| KR | 1020150139635 A | 12/2015 |
| KR | 1020160099478 A | 8/2016 |
| KR | 1020170134045 A | 12/2017 |

* cited by examiner

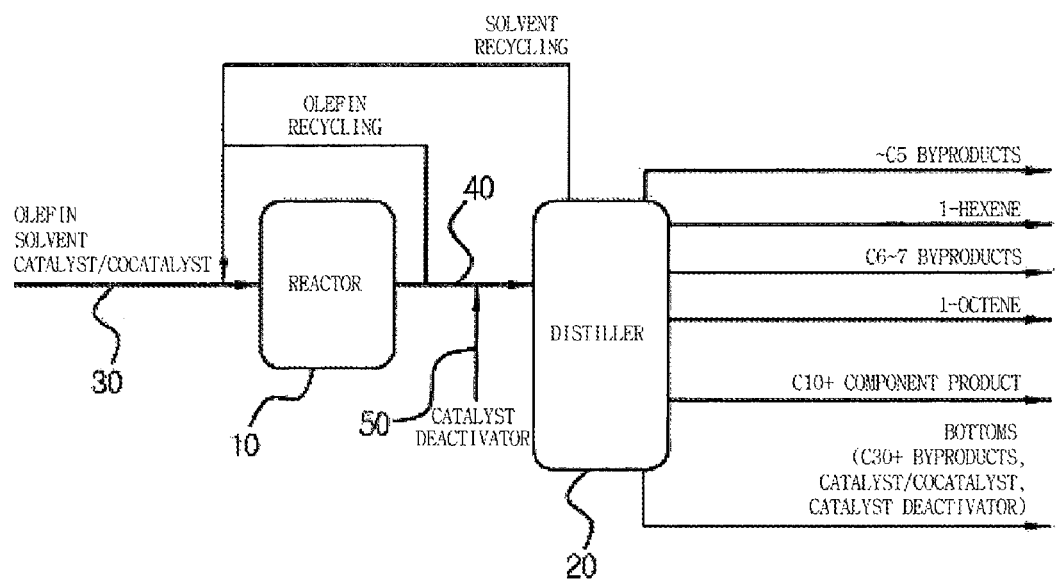

METHOD OF OLEFIN OLIGOMERIZATION

CROSSED-REFERENCE TO RELATED APPLICATIONS

This application is the United States national phase of International Application No. PCT/KR2018/008102 filed Jul. 18, 2018, and claims priority to Korean Patent Application No. 10-2017-0127147 filed Sep. 29, 2017, the disclosures of which are hereby incorporated by reference in their entirety.

TECHNICAL FIELD

The present invention relates to a method for oligomerizing olefins, and more particularly, to a method for oligomerizing olefins capable of achieving a high added value.

BACKGROUND ART

Ethylene is a raw material used as a basic material in the chemical industry to such an extent that its production and consumption are considered as indicators of the chemical industry scale of a country. Typically, ethylene has been used as a monomer for preparing polymers such as polyethylene, and the like. In some cases, linear alpha olefins (LAOs) having an approximately C4-C40 carbon length (or chain) are prepared by adjusting a degree of polymerization of ethylene, and thus are used to prepare a variety of chemicals.

The reason why an LAO preparation technique is important is that LAO is a chemical that does not contain sulfur and nitrogen derived from crude oil. Typically, since crude oil contains impurities such as sulfur and nitrogen components in amounts of several percent by weight, it is difficult to directly prepare chemicals composed of pure hydrocarbons without such impurities.

However, ethylene resulting from a catalytic cracking reaction of crude oil may be converted into LAOs, which are in turn converted into desired chemicals, thereby obtaining chemicals composed of pure hydrocarbons without impurities.

An ethylene polymerization reaction is mainly carried out using a batch reactor under air-sensitive conditions in the presence of a metallocene catalyst. Because the metallocene catalyst is a catalyst that has a very strong single acid site, ethylene is selectively polymerized at the single acid site of the catalyst. Due to such properties, a polymer is linearly grown at the acid site of the catalyst. As a result, olefins produced by an LAO preparation reaction have a linear alpha-olefin structure having an even number of carbon atoms because ethylene is used as a monomer.

Linear alpha olefins produced by an LAO preparation process exhibit distinct physical properties depending on the number of carbon atoms thereof, and chemicals prepared therefrom also have distinct physical properties depending on the type of LAO source materials. For example, C4 LAOs obtained by polymerizing two ethylene monomers are present in a gas phase, and polymers resulting from the polymerization thereof have an excessive amount of intramolecular branches, which makes it difficult to apply to a specific product, for example, a lube base oil. Meanwhile, even when C6 LAOs obtained by polymerizing three ethylene monomers are also converted into polymers, it is difficult to apply such polymers to a lube base oil, and the like because the polymers have many intramolecular branches. However, when ethylene is copolymerized with a C6 LAO, an ethylene-1-hexene copolymer having different physical properties from conventional polyethylene may be prepared. C8 LAOs obtained by polymerizing four ethylene monomers may be applied to a Group IV lube base oil via polymerization, and may be used to prepare a copolymer with ethylene, as in the C6 LAOs. Also, C10-C12 LAOs are polymerized, and thus mainly used as the Group IV base oil, and C14-C16 LAOs are reacted with amine or succinic acid so that the resulting reaction products can be applied to various functional chemicals, or can be mixed and applied to inexpensive drilling fluids, and the like. Also, C18 or more LAOs may be used in the form of an additive or wax for lubricants.

That is, the C18 or more high-carbon LAOs as well as approximately C6-C12 LAOs also have a high possibility for application. In this case, the LAOs need to be also separated with high purity in order to achieve a high added value of an ethylene oligomerization process.

Meanwhile, 2-ethylhexanol, pentanol, or the like has been commonly used as the catalyst deactivator for suppressing side reactions at the rear end of the reactor after the ethylene oligomerization reaction. They have good catalyst deactivation efficiency. However, they have a problem in that, when they are distilled at the latter part of the process, it is difficult to separate them from certain LAO components.

As a specific example, because 2-ethylhexanol has a problem in that it is not easily phase-separated from C10 LAOs, an additional reactor is needed or severe reaction conditions are required in order to separate the C10 LAOs from the oligomerization reaction product, resulting in increased processing costs as well as degraded separation efficiency.

Accordingly, there is a need for a process of preparing a linear alpha olefin by an ethylene oligomerization reaction capable of separating LAOs, which have a wide range of carbon atoms in the reaction products, with high separation efficiency while ensuring sufficient catalyst deactivation after the reaction.

DISCLOSURE

Technical Problem

An object of the present invention is to provide a method for preparing a linear alpha olefin (LAO) from olefins capable of achieving a high added value of a process by suppressing unnecessary side reactions at the rear end of a reactor to prepare linear alpha olefins with high purity and yield and simultaneously separating C10 or more high-carbon LAOs with high separation efficiency.

Technical Solution

In one general aspect, a method for oligomerizing olefins includes: introducing an oligomerization transition metal catalyst, an olefin monomer, and a solvent into a reactor and performing an olefin oligomerization reaction to produce oligomers; introducing a catalyst deactivator to a reaction product of the oligomerization reaction to deactivate the catalyst, wherein the catalyst deactivator includes one or more functional groups containing at least one selected from the group consisting of oxygen, phosphorus, nitrogen, and sulfur, and has a number average molecular weight of 400 or more; separating the oligomers by distillation in a distiller; and separating the catalyst deactivator through the bottom end of the distiller.

The number average molecular weight of the catalyst deactivator may be greater than or equal to 600.

The catalyst deactivator may have 31 or more carbon atoms based on the number average molecular weight thereof.

The catalyst deactivator may be a phosphine-based compound, an amine-based compound, a thiol-based compound, an ether-based compound, an ester-based compound, carboxylic acid, a ketone-based compound, or an alcohol-based compound.

The catalyst deactivator may be represented by the following Formula 1:

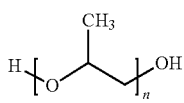

[Formula 1]

(wherein n ranges from 11 to 170).

1-Octene may be included at 30% by weight or more, based on 100% by weight of linear alpha olefins in the reaction product of the oligomerization reaction.

The cocatalyst may be further introduced when the oligomerization transition metal catalyst, the olefin monomer, and the solvent are introduced into the reactor to perform the olefin oligomerization reaction.

The cocatalyst may be an organoaluminum compound, an organoaluminoxane, an organoboron compound, or a mixture thereof.

An amount of the introduced catalyst deactivator may be in a range of 1.5 to 20 times higher than the total number of moles of aluminum, boron, or a combination thereof in the cocatalyst based on the number of moles.

According to the method for oligomerizing olefins according to one aspect of the present invention, in the separating of the oligomers, the oligomers may be separated into C5 or less oligomers; 1-hexene; C6 other than the 1-hexene, and C7 oligomers; 1-octene; and C8 other than the 1-octene, and C9-C20 oligomers.

The transition metal catalyst may be represented by $ML^1(L^2)_p(X)_q$ or $M_2X^1{}_2L^1{}_2(L^2)_y(X)_z$ (wherein M is a transition metal, $L^1$ is a heteroligand, $L^2$ is an organic ligand, X and $X^1$ are each independently a halogen, p is an integer of 0 or 1 or more, q is an integer of (oxidation number of M−p), y is an integer of 2 or more, and z is an integer of (2× oxidation number of M)−y).

The olefin monomer may be ethylene, and the oligomers may include a mixture of C4-C40 linear alpha olefins.

Advantageous Effects

According to the method for oligomerizing olefins according to one aspect of the present invention, linear alpha olefins can be produced with high purity and yield by suppressing unnecessary side reactions at the rear end of a reactor or at the end of a reaction.

Also, process energy can be reduced and process efficiency can be enhanced by separating the C10 or more high-carbon LAOs with high separation efficiency, and a high added value can be achieved in terms of an LAO preparation process as well.

DESCRIPTION OF DRAWING

FIG. 1 is a schematic diagram of a plant capable of performing a method for oligomerizing olefins according to one aspect of the present invention.

BEST MODE

Unless particularly defined otherwise, all terms (including technical and scientific terms) used herein may be used as the same meaning as commonly understood by one of ordinary skill in the art to which this invention belongs. Throughout the specification, a certain part "including" a certain element signifies that the certain part may further include, instead of excluding, another element unless particularly indicated otherwise. Also, the singular forms "a," "an," and "the" include plural referents unless the context clearly dictates otherwise.

In reaction products of an olefin oligomerization reaction, low-carbon linear alpha olefins (LAOs) and C18 or more high-carbon LAOs also have a high possibility for application. In this case, the LAOs need to be also separated with high purity in order to achieve a high added value of an olefin oligomerization process.

One aspect of the present invention provides a method for oligomerizing olefins capable of enhancing separation efficiency of C10 or more, specifically C18 or more high-carbon LAOs to achieve a high added value of an olefin oligomerization process.

Specifically, one aspect of the present invention provides a method for oligomerizing olefins, which includes introducing an oligomerization transition metal catalyst, an olefin monomer, and a solvent into a reactor and performing an olefin oligomerization reaction to produce oligomers; introducing a catalyst deactivator to a reaction product of the oligomerization reaction to deactivate the catalyst, wherein the catalyst deactivator includes one or more functional groups containing at least one selected from the group consisting of oxygen, phosphorus, nitrogen, and sulfur, and has a number average molecular weight of 400 or more; separating the oligomers by distillation in a distiller; and separating the catalyst deactivator through the bottom end of the distiller.

In the method for oligomerizing olefins according to one aspect of the present invention, the catalyst deactivator, which has a number average molecular weight ($M_n$) of 400 or more, and includes one or more functional groups containing any one selected from the group consisting of oxygen, phosphorus, nitrogen, and sulfur, may be added at the end of a reaction. Therefore, reaction selectivity of the oligomerization reaction may be improved. The reaction selectivity of the oligomerization reaction may be evaluated using the purity of 1-octene in the reaction product, and 1-octene is an expensive material that may be applied to Group IV lube base oil via polymerization and may be used to prepare a copolymer with ethylene, as in the C6 LAOs. Therefore, the higher purity of 1-octene makes it possible to achieve a high added value of the reaction.

Also, the catalyst deactivator, which has a number average molecular weight ($M_n$) of 400 or more, and includes one or more functional groups containing any one selected from the group consisting of oxygen, phosphorus, nitrogen, and sulfur, may be added, during an oligomerization reaction, to suppress side reactions that occur unnecessarily at the rear end of the reactor or at the end of the reaction, thereby improving the yield of C4-C40 linear alpha olefins. Also, when such a catalyst deactivator is used to separate the produced linear alpha olefin by distillation, the final yield of the produced linear alpha olefins may be further improved as a result of improvement of efficiency of separation of the linear alpha olefins from the catalyst deactivator. More specifically, when such a catalyst deactivator is used, the catalyst deactivator may be separated through the bottom end of the distiller in a distillation procedure, and low-carbon linear alpha olefins, and C10 or more, and specifically C18 or more high-carbon linear alpha olefins may be easily separated through the top or middle portion of the distiller.

When the catalyst deactivator has a higher boiling point, the linear alpha olefins are considered to be easily separated during a distillation procedure. However, an organic compound catalyst deactivator may decompose before the catalyst deactivator reaches a boiling point, and a separation pattern may vary upon distillation due to the chemical interaction such as physical bonding with a catalyst or a cocatalyst or complex formation during a deactivation procedure.

Accordingly, it was confirmed that, although the catalyst deactivator simply has a higher boiling point, separation of the linear alpha olefins may not be considered to be easy, and the catalyst deactivator, which has a number average molecular weight ($M_n$) of 400 or more and includes one or more functional groups containing any one selected from the group consisting of oxygen, phosphorus, nitrogen, and sulfur, is used in the method for oligomerizing olefins according to the present invention to improve separation efficiency of the catalyst deactivator from the linear alpha olefins in the oligomerization reaction product.

The number average molecular weight of the catalyst deactivator may be specifically greater than or equal to 600, 700, or 1,000.

As a result, a problem of needing an additional reactor or requiring severe reaction conditions in order to separate desired linear alpha olefins from the catalyst deactivator, and the like in the oligomerization reaction product may be solved. Also, separation efficiency of the linear alpha olefins may be improved to remarkably reduce process energy and a process time, and low-carbon linear alpha olefins and C10 or more, and more specifically C18 or more linear alpha olefins may also be easily separated, thereby further achieving a high added value of an olefin oligomerization process.

The upper limit of the number average molecular weight of the catalyst deactivator may be less than or equal to 10,000, 5,000, or 2,000, but the present invention is not limited thereto.

In the present invention, the linear alpha olefins in the reaction product of the oligomerization reaction may be C4-C40 linear alpha olefins, and more specifically C4-C30 or C4-C20 linear alpha olefins. Even more specifically, the linear alpha olefins may include 30% by weight or more, or 50% by weight or more of 1-octene. Because 1-octene has a wide range of applications and is expensive, 1-octene may enhance a high added value of the olefin oligomerization process when 1-octene is included in this range as described above. Also, 1-octene has an advantage in that, because a content of 1-octene in the linear alpha olefins is high, only 1-octene may be easily separated with high purity even when the high-carbon linear alpha olefins are mixed with the reaction product, but the present invention is not particularly limited thereto.

The catalyst deactivator may be a C30 or more, C31 or more, C36 or more, C50 or more, or C51 or more compound. Within this range, the catalyst deactivator may have suitable carbon atoms for separation from the linear alpha olefins, and other factors such as interaction with the catalyst/cocatalyst in a catalyst deactivation procedure, and the like act together to improve separation efficiency between the oligomerization reaction product and the catalyst deactivator.

The catalyst deactivator may include one or more functional groups containing any one selected from the group consisting of oxygen, phosphorus, nitrogen, and sulfur. In a specific aspect, the catalyst deactivator may include a functional group(s) of one type containing one of the four elements, or may include a functional group(s) of two or more types containing one of the four elements. This is given by way of illustration, but the present invention is not limited thereto.

Specific types of the catalyst deactivator may be a C31 or more phosphine-based compound, a C31 or more amine-based compound, a C31 or more thiol-based compound, a C31 or more alcohol-based compound, a C31 or more ether-based compound, a C31 or more ester-based compound, C31 or more carboxylic acid, or a C31 or more ketone-based compound.

More specifically, the catalyst deactivator may be a C31 or more phosphine-based compound, a C31 or more amine-based compound, a C31 or more thiol-based compound, or a C31 or more alcohol-based compound.

Even more specifically, the catalyst deactivator may be polypropylene glycol (PPG) represented by the following Formula 1:

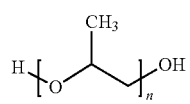

[Formula 1]

(wherein n ranges from 11 to 170).

In Formula 1, n may more specifically range from 12 to 150, from 17 to 130, from 17 to 110, from 17 to 35, or from 16 to 35.

The catalyst deactivator of the present invention is not particularly limited, and this polypropylene glycol compound may be preferred because the compound has a good catalyst deactivation effect, compared to a polyethylene glycol compound in the alcohol-based compound, and may be easily separated from the linear alpha olefins in the reaction product of the olefin oligomerization reaction.

In the method for oligomerizing olefins according to one aspect of the present invention, the cocatalyst may be further introduced when the oligomerization transition metal catalyst, the olefin monomer, and the solvent are introduced into the reactor to perform an olefin oligomerization reaction.

The cocatalyst may be an organoaluminum compound, an organoaluminoxane, an organoboron compound, or a mixture thereof.

The organoaluminum compound may be an $AlR_3$ compound (wherein R is each independently a (C1-C12)alkyl, a (C2-C10)alkenyl, a (C2-C10)alkynyl, a (C1-C12)alkoxy, or a halogen), or $LiAlH_4$, but the present invention is not limited thereto.

More specifically, the organoaluminum compound may be one selected from trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride, or a mixture thereof, but the present invention is not limited thereto.

The organoaluminoxane may be an oligomer compound that may be prepared by adding water to trimethylaluminum, but the present invention is not limited thereto. The aluminoxane oligomer compound thus prepared may be linear, cyclic, cage or a mixture thereof.

Specifically, the organoaluminoxane may be selected from alkylaluminoxanes, for example, methylaluminoxane (MAO), ethylaluminoxane (EAO), tetraisobutylaluminoxane (TIBAO), and isobutylaluminoxane (IBAO), as well as modified alkyl aluminoxanes, for example, modified methylaluminoxane (MAO). The modified methylaluminoxane (manufactured by Akzo Nobel) may include a mixed alkyl group such as an isobutyl or n-octyl group in addition to a methyl group, but the present invention is not limited thereto.

More specifically, the organoaluminoxane may be one selected from methylaluminoxane (MAO), modified methylaluminoxane (MAO), ethylaluminoxane (EAO), tetraisobutylaluminoxane (TIBAO), and isobutylaluminoxane (IBAO), or a mixture thereof, but the present invention is not limited thereto.

The organoboron compound may be boroxine, $NaBH_4$, triethylborane, triphenylborane, a triphenylborane ammonia complex compound, tributylborate, triisopropylborate, tris(pentafluorophenyl)borane, trityl(tetrapentafluorophenyl)borate, dimethylphenylammonium(tetrapentafluorophenyl)borate, diethylphenylammonium(tetrapentafluorophenyl)borate, methyldiphenylammonium(tetrapentafluorophenyl)borate, or ethyldiphenylammonium(tetrapentafluorophenyl)borate, and these organoboron compounds may be used as a mixture with the organoaluminum compound or the organoaluminoxane, but the present invention is not limited thereto.

In the introducing of the catalyst deactivator to deactivate the catalyst, an amount of the introduced catalyst deactivator may be in a range of 1.5 to 20 times higher than the total number of moles of aluminum, boron, or a combination thereof in the cocatalyst based on the number of moles. When the catalyst deactivator is introduced in this range, sufficient deactivation of the catalyst may occur, and the catalyst deactivator may be easily separated from the linear alpha olefins in the oligomerization reaction product, but the present invention is not particularly limited thereto. More specifically, the amount of the introduced catalyst deactivator may be 1.5 times to 10 times, 2 times to 8 times, or 3 times to 7 times higher than the total number of moles of aluminum, boron, or a combination thereof in the cocatalyst based on the number of moles.

The method for oligomerizing olefins according to one aspect of the present invention may be performed in a plant including any type of a reactor. FIG. 1 is a schematic diagram of a plant capable of performing a method for oligomerizing olefins according to one aspect of the present invention. Hereinafter, the method for oligomerizing olefins according to one aspect of the present invention will be described in further detail with reference to FIG. 1. However, it should be understood that the present invention is not limited to FIG. 1, and may be freely modified and put into practice by those skilled in the art without departing from the technical scope of the present invention.

A plant may include a reactor 10 configured to perform oligomerization, a feed line 30 configured to feed an olefin and a catalyst composition into the reactor 10, an outlet line 40 configured to allow an oligomerization reaction product to flow out of the reactor 10, a catalyst deactivator feed line 50 configured to introduce a catalyst deactivator through the outlet line 40, and a distiller 20 configured to separate the oligomerization reaction product. In this case, the catalyst composition is an olefin oligomerization catalyst composition disclosed in the present invention, and may include a transition metal source and a heteroatom ligand, or an oligomerization transition metal catalyst/cocatalyst prepared therefrom.

The reactor 10 may include a batch-type reactor, a semi-batch-type reactor, and a continuous reactor, but the present invention is not limited thereto.

The distiller 20 is not limited to certain types of distillers, and the number of distillation column stages may be adjusted when necessary. Also, a distillation method is not limited to certain distillation methods, and proper distillation methods may be used when necessary. FIG. 1 shows that one distiller is included, but a number of distillers may be used when necessary.

When the reaction product in which the catalyst is deactivated is distilled according to the method for oligomerizing olefins according to one aspect of the present invention, the catalyst deactivator may be separated through the bottom end of the distiller 20, and thus may be separated from the resulting oligomers. In this case, additionally produced oligomers may be separated into C5 or less oligomers, 1-hexene, C6-C7 oligomers, 1-octene, and C10-C20 oligomers, which may then be manufactured according to purposes thereof, thereby achieving a high added value of an oligomerization process. A separation pattern of such oligomers is given by way of illustration, but the present invention is not particularly limited thereto.

In the method for oligomerizing olefins according to one aspect of the present invention, the olefin monomer may be ethylene, and the oligomers may include a mixture of C4-C40 linear alpha olefins, but the present invention is not particularly limited thereto.

In the method for oligomerizing olefins according to one aspect of the present invention, when the oligomerization transition metal catalyst, the olefin monomer, and the solvent are introduced into the reactor, the solvent may be an inert solvent. That is, any inert solvent that does not react with the oligomerization transition metal catalyst, the cocatalyst, and the catalyst deactivator may be used as the solvent, and the inert solvent may include an aliphatic hydrocarbon. The aliphatic hydrocarbon includes saturated aliphatic hydrocarbons, that is, a linear saturated aliphatic hydrocarbon represented by $C_nH_{2n+2}$ (wherein n is an integer ranging from 1 to 15), an alicyclically saturated aliphatic hydrocarbon represented by $C_mH_{2m}$ (wherein m is an integer ranging from 3 to 8), and a saturated aliphatic hydrocarbon substituted with one or two or more lower alkyl groups having 1 to 3 carbon atoms. Examples of the solvent specifically listed herein may include one or more selected from hexane, heptane, octane, nonene, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but the present invention is not limited thereto.

Also, in the method for oligomerizing olefins according to one aspect of the present invention, the oligomerization reaction may be performed at a temperature of 0 to 200° C., specifically a temperature of 15 to 130° C., and even more specifically a temperature of 30 to 70° C., and may be performed at a reaction pressure, for example, a pressure of an atmospheric pressure to 100 bar, and specifically a pressure of an atmospheric pressure to 80 bar, but the present invention is not limited thereto.

Hereinafter, an olefin oligomerization catalyst of the present invention will be described in detail. However, it should be understood that the oligomerization catalyst of the present invention is not particularly limited thereto.

The olefin oligomerization catalyst of the present invention may be directly prepared and used, or commercially available oligomerization catalysts may be used herein. Also, components that may be used to prepare an oligomerization catalyst, that is, a transition metal source and a heteroatom ligand may be used.

The transition metal source according to one exemplary embodiment of the present invention may be an inorganic transition metal salt, an organic transition metal salt, a transition metal coordination compound, or a complex of the transition metal with an organic metal, and a transition metal of the transition metal source may be a Group IV, V or VI transition metal, and specifically chromium, molybdenum, tungsten, titanium, tantalum, vanadium, or zirconium, and preferably chromium.

By way of example, a transition metal of the transition metal source may be bound with various organic ligands, and such organic ligands may be selected from the following structures.

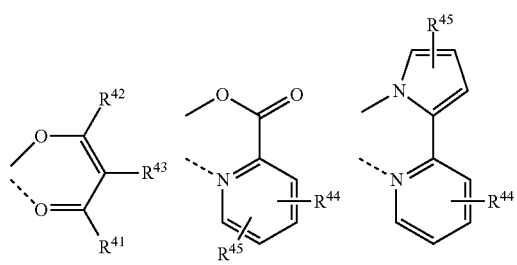

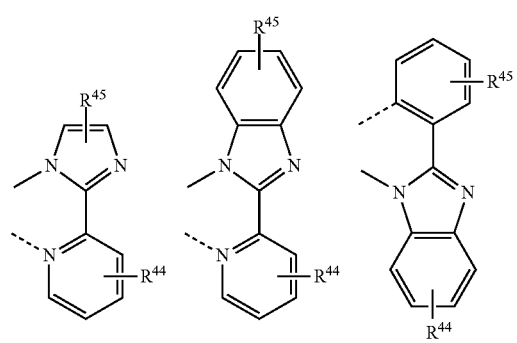

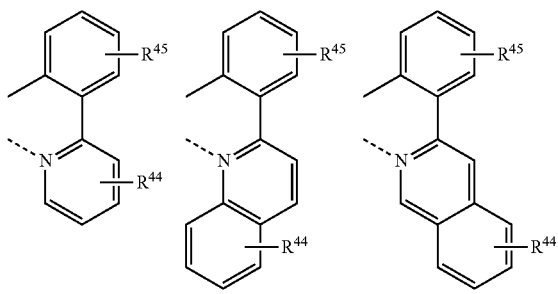

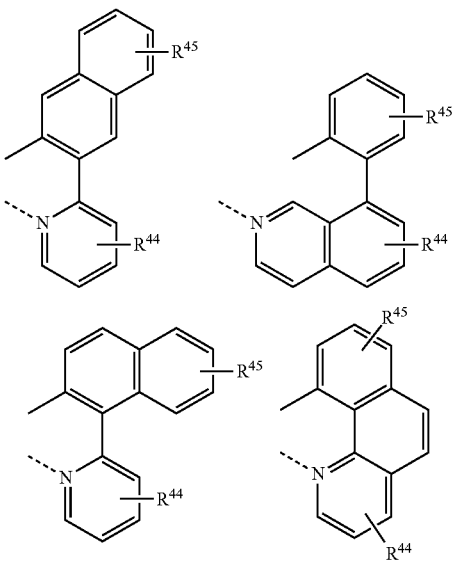

(wherein $R^{41}$ to $R^{45}$ are each independently a hydrocarbyl, a substituted hydrocarbyl, a heterohydrocarbyl, or a substituted heterohydrocarbyl).

The organic ligand may be preferably an acetylacetonato-based ligand represented by the following Formula 2:

[Formula 2]

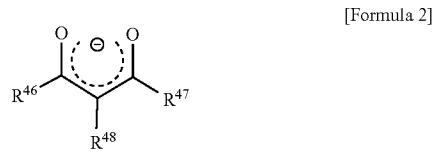

(wherein $R^{46}$ to $R^{48}$ are each independently hydrogen, a halogen, a (C6-C20)aryl, a (C6-C20)ar(C1-C10)alkyl, a (C1-C10)alkyl, a halo(C1-C10)alkyl, a (C6-C20)ar(C2-C10)alkenyl, a (C2-C10)alkenyl, a (C6-C20)ar(C2-C10)alkynyl, a (C2-C10)alkynyl, a (C1-C10)alkoxy, a (C6-C20)aryloxy, a (C1-C10)alkylcarbonyloxy, a (C2-C10)alkenylcarbonyloxy, a (C2-C10)alkynylcarbonyloxy, a (C3-C7)cycloalkyl, a (C1-C10)alkylsilyl, a (C2-C10)alkenylsilyl, a (C2-C10)alkynylsilyl substituted with fluorine, a (C6-C20)arylsilyl, a (C3-C20)heteroaryl, or a 5- to 7-membered heterocycloalkyl; and the aryl, the aralkyl, the alkyl, the aralkenyl, the alkenyl, the aralkynyl, the alkynyl, the alkoxy, the aryloxy, the cycloalkyl, the heteroaryl, and the heterocycloalkyl of $R^{46}$ to $R^{48}$ may be further substituted with one or more selected from a (C1-C10)alkyl, a (C2-C10)alkenyl, a (C2-C10)alkynyl, a (C1-C10)alkoxy, a (C6-C20)aryl, a (C6-C20)aryloxy, and a halogen).

Preferably, $R^{46}$ and $R^{47}$ in Formula 2 may be each independently hydrogen, a halogen, or a halo(C1-C10)alkyl, and $R^{48}$ may be hydrogen, or a (C1-C10)alkyl.

The acetylacetonato-based ligand of Formula 2 according to one exemplary embodiment of the present invention may be selected from the following structures, but the present invention is not limited thereto.

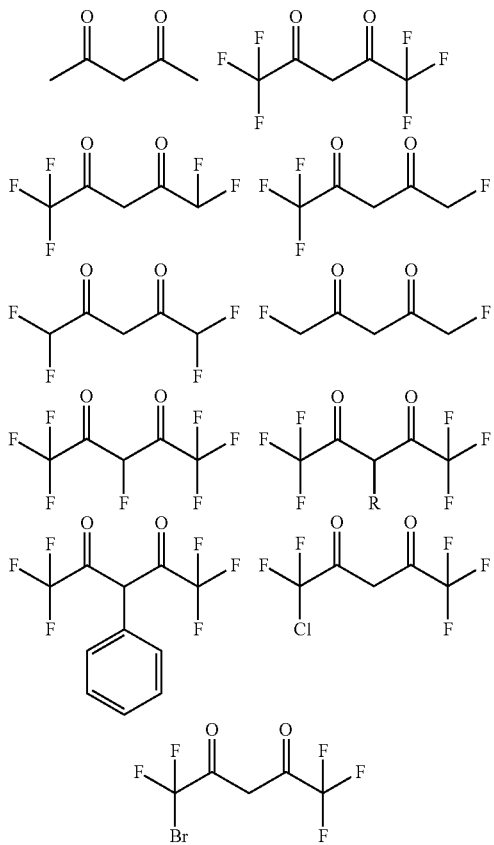

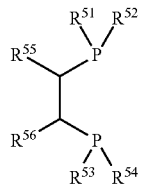

[Formula 3]

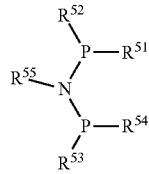

[Formula 4]

When the transition metal as one specific example of the transition metal source is chromium, the transition metal may include one or two or more selected from chromium (III) acetylacetonate, chromium(III) chloride, chromium(III) naphthenate, chromium(III) 2-ethylhexanoate, chromium (III) acetate, chromium(III) 2,2,6,6-tetramethylheptadionate, chromium(III) octanoate, and chromium hexacarbonyl. Preferably, the transition metal may be chromium(III) acetylacetonate, or chromium(III) chloride.

Preferably, the heteroatom ligand according to one exemplary embodiment of the present invention may be $(R)_nB$—C-D$(R)_m$ (wherein B and D are independently any one selected from phosphorus, arsenic, antimony, oxygen, bismuth, sulfur, selenium, and nitrogen, C is a linking group between B and D, R is the same as or different from each other, and is each independently selected from a hydrocarbyl group, a heterohydrocarbyl group, a substituted hydrocarbyl group, and a substituted heterohydrocarbyl group, n and m each may be determined from the valence and oxidation state of either B or D, respectively, B and D are preferably independently phosphorus, C may be a linking group between B and D, that is, alkylene or N(R') (wherein R' is an alkyl), R is the same as or different from each other, and is each independently selected from a hydrocarbyl group, a heterohydrocarbyl group, a substituted hydrocarbyl group, and a substituted heterohydrocarbyl group, and n and m each may be determined from the valence and oxidation state of either B or D, respectively).

The heteroatom ligand may have a P—C—C—P backbone structure represented by the following Formula 3, or a P—N—P backbone structure represented by the following Formula 4, but the present invention is not limited thereto:

(wherein $R^{51}$ to $R^{54}$ are each independently a hydrocarbyl, a substituted hydrocarbyl, a heterohydrocarbyl, or a substituted heterohydrocarbyl; and $R^{55}$ and $R^{56}$ are each independently a hydrocarbyl or a substituted hydrocarbyl, or $R^{55}$ and $R^{56}$ may be taken together via hydrocarbylene, substituted hydrocarbylene, heterohydrocarbylene, or substituted heterohydrocarbylene to form a ring).

$R^{51}$ to $R^{54}$ in Formulas 3 and 4 are each independently a (C6-C20)aryl, a (C6-C20)ar(C1-C10)alkyl, a (C6-C20)ar(C2-C10)alkenyl, a (C6-C20)ar(C2-C10)alkynyl, a (C1-C10)alkyl, a (C2-C10)alkenyl, a (C2-C10)alkynyl, a (C1-C10)alkoxy, a (C6-C20)aryloxy, a (C1-C10)alkoxycarbonyl, a (C1-C10)alkylcarbonyloxy, a (C2-C10)alkenylcarbonyloxy, a (C2-C10)alkynylcarbonyloxy, an aminocarbonyl, a (C1-C10)alkylcarbonylamino, a (C2-C10)alkenylcarbonylamino, a (C2-C10)alkynylcarbonylamino, a (C3-C7)cycloalkyl, a thio(C1-C10)alkyl, a thio(C2-C10)alkenyl, a thio(C2-C10)alkynyl, a (C1-C10)alkylsilyl, a (C2-C10)alkenylsilyl, a (C2-C10)alkynylsilyl, a (C6-C20)arylsilyl, a (C3-C20)heteroaryl, a 5- to 7-membered heterocycloalkyl, or —$NR^{61}R^{62}$, wherein $R^{61}$ and $R^{62}$ are each independently a (C1-C10)alkyl, a (C2-C10)alkenyl, a (C2-C10)alkynyl, a (C6-C20)aryl, a di(C1-C10)alkylamino, a di(C2-C10)alkenylamino, or a di(C2-C10)alkynylamino;

$R^{55}$ and $R^{56}$ are each independently a (C6-C20)aryl, a (C6-C20)ar(C1-C10)alkyl, a (C6-C20)ar(C2-C10)alkenyl, a (C6-C20)ar(C2-C10)alkynyl, a (C1-C10)alkyl, a (C2-C10)alkenyl, a (C2-C10)alkynyl, a (C3-C7)cycloalkyl, a (C3-C20)heteroaryl, a 5- to 7-membered heterocycloalkyl, a (C1-C10)alkoxy, a (C6-C20)aryloxy, a (C1-C10)alkoxycarbonyl, a (C1-C10)alkylcarbonyloxy, a (C2-C10)alkenylcarbonyloxy, a (C2-C10)alkynylcarbonyloxy, an aminocarbonyl, a (C1-C10)alkylcarbonylamino, a (C2-C10)alkenylcarbonylamino, a (C2-C10)alkynylcarbonylamino, a di(C1-C10)alkylamino, a di(C2-C10)alkenylamino, a di(C2-C10)alkynylamino, a (C1-C10)alkylsilyl, a (C2-C10)alkenylsilyl, a (C2-C10)alkynylsilyl, or a (C6-C20)arylsilyl, or $R^{55}$ and $R^{56}$ may be taken together via a (C3-C10)alkylene or a (C3-C10)alkenylene to form a ring; and the aryl, the aralkyl, the aralkenyl, the aralkynyl, the alkyl, the alkenyl, the alkoxy, the aryloxy, the alkoxycarbonyl, the alkylcarbonyloxy, the alkenylcarbonyloxy, the alkynylcarbonyloxy, the cycloalkyl, the heteroaryl, or the heterocycloalkyl of $R^{51}$ to $R^{54}$, and the aryl, the aralkyl, the aralkenyl, the aralkynyl, the alkyl, the alkenyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, the alkynylcarbonylamino, the dialkylamino, the dialkenylamino, the dialkynylamino, the alkylsilyl, the alkenylsilyl, the alkynylsilyl, or the arylsilyl of $R^{55}$ and $R^{56}$ may be further substituted with one or more selected from a (C1-C10)alkyl, a (C2-C10)alkenyl, a (C2-C10)alkynyl, a (C1-C10)alkoxy, a (C6-C20)aryloxy, a di(C1-C10)alkylamino, a di(C2-C10) alkenylamino, a di(C2-C10)alkynylamino, and a halogen.

Preferably, $R^{51}$ to $R^{54}$ in Formulas 3 and 4 may be each independently a (C6-C20)aryl; and $R^{55}$ and $R^{56}$ may be each independently a (C1-C10)alkyl.

Specifically, in Formulas 3 and 4, $R^{51}$ to $R^{54}$ are each independently phenyl, benzyl, biphenyl, naphthyl, anthracenyl, mesityl, xylyl, methyl, ethyl, ethenyl, ethinyl, n-propyl, i-propyl, propenyl, propynyl, n-butyl, t-butyl, butenyl, butynyl, methylphenyl, ethylphenyl, methoxyphenyl, ethoxyphenyl, isopropylphenyl, isopropoxyphenyl, t-butylphenyl, cumyl, methoxy, ethoxy, phenoxy, tolyloxy, dimethylaminophenyl, cyclopropyl, cyclobutyl, cyclopentyl, cyclohexyl, methylcyclohexyl, ethylcyclohexyl, isopropylcyclohexyl, dimethylamino, thiomethyl, trimethylsilyl, or dimethylhydrazyl; and $R^{55}$ and $R^{56}$ are each independently methyl, ethyl, ethenyl, ethinyl, n-propyl, i-propyl, propenyl, propynyl, n-butyl, t-butyl, i-butyl, butenyl, butynyl, phenyl, benzyl, tolyl, xylyl, methoxy, ethoxy, phenoxy, methylamino, or dimethylamino, or $R^{55}$ and $R^{56}$ may be taken together via propylene, butylene, pentylene, or butenylene to form a 5- to 7-membered ring.

The ligand having the P—C—C—P backbone structure of Formula 3 may be selected from (phenyl)₂P—CH(methyl) CH(methyl)-P(phenyl)₂, (4-methoxyphenyl)₂P—CH (methyl)CH(methyl)-P(4-methoxyphenyl)₂, (4-methylphenyl)₂P—CH(methyl)CH(methyl)-P(4-methylphenyl)₂, (4-ethylphenyl)₂P—CH(methyl)CH(methyl)-P(phenyl)₂, (2-ethylphenyl)₂P—CH(methyl)CH(methyl)-P(2-ethylphenyl)₂, (2-isopropylphenyl)₂P–CH(methyl)CH(methyl)P-(2-isopropylphenyl)₂, (2-methylphenyl)₂P—CH(methyl)CH (methyl)P-(2-methylphenyl)₂, (2-ethylphenyl)₂P—CH (methyl)CH(methyl)-P(phenyl)₂, (3-methoxyphenyl)₂P—CH(methyl)CH(methyl)-P(3-methoxyphenyl)₂, (4-ethoxyphenyl)₂P—CH(methyl)CH(methyl)-P(2-ethoxyphenyl)₂, (4-dimethylaminophenyl)₂P—CH(methyl)CH (methyl)-P(4-dimethylaminophenyl)₂, (4-ethylcyclohexyl)₂ P—CH(methyl)CH(methyl)-P(4-ethylcyclohexyl)₂, (2-methoxyphenyl)₂P—CH(methyl)CH(methyl)-P(2-methoxyphenyl)₂, (2-ethoxyphenyl)₂P—CH(methyl)CH (methyl)-P(2-ethoxyphenyl)₂, (2-dimethylaminophenyl)₂ P—CH(methyl)CH(methyl)-P(2-dimethylaminophenyl)₂, (2-ethylcyclohexyl)₂P—CH(methyl)CH(methyl)-P(2-ethylcyclohexyl)₂, (4-ethylphenyl)₂P—CH(ethyl)CH(methyl)-P (4-ethylphenyl)₂, (4-methoxyphenyl)₂P—CH(ethyl)CH (methyl)-P(phenyl)₂, (2-ethylphenyl)₂P—CH(ethyl)CH (methyl)-P(2-ethylphenyl)₂, (4-ethylphenyl)₂P—CH(ethyl) CH(ethyl)-P(4-ethylphenyl)₂, (phenyl)₂P—CH(ethyl)CH (ethyl)-P(phenyl)₂, (2-ethylphenyl)₂P—CH(ethyl)CH (ethyl)-P(2-ethylphenyl)₂, (phenyl)₂P—CH(isopropyl)CH (methyl)-P(phenyl)₂, (4-methoxyphenyl)₂P—CH (isopropyl)CH(methyl)-P(4-methoxyphenyl)₂, (4-ethylphenyl)₂P—CH(isopropyl)CH(methyl)-P(4-ethylphenyl)₂, (2-ethylphenyl)₂P—CH(isopropyl)CH(methyl)-P(2-ethylphenyl)₂, (phenyl)₂P—CH(n-propyl)CH(methyl)-P(phenyl)₂, (4-methoxyphenyl)₂P—CH(n-propyl)CH (methyl)-P(4-methoxyphenyl)₂, (4-ethylphenyl)₂P—CH(n-propyl)CH(methyl)-P(4-ethylphenyl)₂, (2-ethylphenyl)₂P—CH(n-propyl)CH(methyl)-P(2-ethylphenyl)₂, (phenyl)₂P—CH(isopropyl)CH(ethyl)-P(phenyl)₂, (4-methoxyphenyl)₂ P—CH(isopropyl)CH(ethyl)-P(4-methoxyphenyl)₂, (4-ethylphenyl)₂P—CH(isopropyl)CH(ethyl)-P(4-ethylphenyl)₂, (2-ethylphenyl)₂P—CH(isopropyl)CH(ethyl)-P(2-ethylphenyl)₂, 1,2-di-(P(phenyl)₂)cyclohexane, 1,2-di-(P(4-methoxyphenyl)₂)cyclohexane, 1,2-di-(P(4-ethylphenyl)₂) cyclohexane, 1,2-di-(P(2-ethylphenyl)₂)cyclohexane, 1,2-di-(P(phenyl)₂)cyclopentane, 1,2-di-(P(4-methoxyphenyl)₂) cyclopentane, 1,2-di-(P(4-ethylphenyl)₂)cyclopentane, 1,2-di-(P(2-ethylphenyl) 2)cyclopentane, (4-ethylphenyl)₂ P—CH (dimethylamino)CH(dimethylamino)-P(4-ethylphenyl)₂, and (2-ethylphenyl)₂P—CH (dimethylamino)CH(dimethylamino)-P(2-ethylphenyl)₂, but the present invention is not limited thereto.

The ligand having the P—N—P backbone structure of Formula 4 may be selected from (phenyl)₂PN(methyl)P (phenyl)₂, (phenyl)₂PN(pentyl)P(phenyl)₂, (phenyl)₂PN (phenyl)P(phenyl)₂, (phenyl)₂PN(p-methoxyphenyl)P(phenyl)₂, (phenyl)₂PN(p-tbutylphenyl)P(phenyl)₂, (phenyl)₂PN ((CH₂)₃—N-morpholine)P(phenyl)₂, (phenyl)₂PN(Si (CH₃)₃)P(phenyl)₂, (((phenyl)₂P)₂NCH₂CH₂) N, (ethyl)₂PN (methyl)P(ethyl)₂, (ethyl)₂PN(isopropyl)P(phenyl)₂, (ethyl) (phenyl)PN(methyl)P(ethyl) (phenyl), (ethyl)(phenyl)PN (isopropyl)P(Phenyl)₂, (phenyl)₂P(=Se)N(isopropyl)P (phenyl)₂, (phenyl)₂PCH₂CH₂P (phenyl)₂, (o-ethylphenyl) (phenyl)PN(isopropyl)P(phenyl)₂, (o-methylphenyl)₂PN (isopropyl)P(o-methylphenyl)(phenyl), (phenyl)₂PN (benzyl)P(phenyl)₂, (phenyl)₂PN(1-cyclohexylethyl)P (phenyl)₂, (phenyl)₂PN [CH₂CH₂CH₂Si(OMe₃)]P (phenyl)₂, (phenyl)₂PN(cyclohexyl)P(phenyl)₂, (phenyl)₂ PN(2-methylcyclohexyl)P(phenyl)₂, (phenyl)₂PN(allyl)P (phenyl)₂, (2-naphthyl)₂PN(methyl)P(2-naphthyl)₂, (p-biphenyl)₂PN(methyl)P(p-biphenyl)₂, (p-methylphenyl)₂PN (methyl)P(p-methylphenyl)₂, (2-thiophenyl)₂PN(methyl)P (2-thiophenyl)₂, (phenyl)₂PN(methyl)N(methyl)P(phenyl)₂, (m-methylphenyl)₂PN(methyl)P(m-methylphenyl)₂, (phenyl)₂PN(isopropyl)P(phenyl)₂, and (phenyl)₂P(=S)N(isopropyl)P(phenyl)₂, but the present invention is not limited thereto.

The heteroatom ligand constituting the olefin oligomerization catalyst according to the present invention may be prepared using various methods known to those skilled in the art.

The olefin oligomerization catalyst according to the present invention may be mononuclear or binuclear. Specifically, the olefin oligomerization catalyst may be represented by $ML^1(L^2)_p(X)_q$ or $M_2X^1{}_2L^1{}_2 (L^2)_y(X)_z$, wherein M is a transition metal, $L^1$ is a heteroligand, $L^2$ is an organic ligand, X and $X^1$ are each independently a halogen, p is an integer of 0 or 1 or more, q is an integer of (oxidation number of M−p), y is an integer of 2 or more, and z is an integer of (2× oxidation number of M)−y−2.

Preferably, the oligomerization catalyst according to one exemplary embodiment of the present invention may be represented by the following Formula 5 or 6, but the present invention is not limited thereto:

[Formula 5]

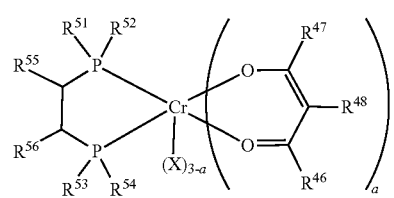

-continued

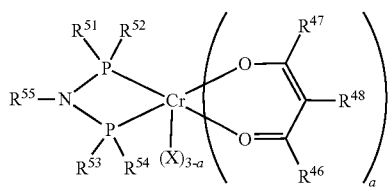

[Formula 6]

(wherein $R^{46}$ to $R^{48}$ are each independently hydrogen, a halogen, a (C6-C20)aryl, a (C6-C20)ar(C1-C10)alkyl, a (C1-C10)alkyl, a halo(C1-C10)alkyl, a (C6-C20)ar(C2-C10)alkenyl, a (C2-C10)alkenyl, a (C6-C20)ar(C2-C10)alkynyl, a (C2-C10)alkynyl, a (C1-C10)alkoxy, a (C6-C20)aryloxy, a (C1-C10)alkylcarbonyloxy, a (C2-C10)alkenylcarbonyloxy, a (C2-C10)alkynylcarbonyloxy, a (C3-C7)cycloalkyl, a (C1-C10)alkylsilyl, a (C2-C10)alkenylsilyl, a (C2-C10)alkynylsilyl, a (C6-C20)arylsilyl, a (C3-C20)heteroaryl, or a 5- to 7-membered heterocycloalkyl;

the aryl, the aralkyl, the alkyl, the aralkenyl, the alkenyl, the aralkynyl, the alkynyl, the alkoxy, the aryloxy, the cycloalkyl, the heteroaryl, and the heterocycloalkyl of $R^{46}$, $R^{47}$, and $R^{48}$ may be further substituted with one or more selected from a (C1-C10)alkyl, a (C2-C10)alkenyl, a (C2-C10)alkynyl, a (C1-C10)alkoxy, a (C6-C20)aryl, a (C6-C20)aryloxy, and a halogen;

$R^{51}$ to $R^{54}$ are each independently a (C6-C20) aryl, a (C6-C20)ar(C1-C10)alkyl, a (C6-C20)ar(C2-C10)alkenyl, a (C6-C20)ar(C2-C10)alkynyl, a (C1-C10)alkyl, a (C2-C10)alkenyl, a (C2-C10)alkynyl, a (C1-C10)alkoxy, a (C6-C20)aryloxy, a (C1-C10)alkoxycarbonyl, a (C1-C10)alkylcarbonyloxy, a (C2-C10)alkenylcarbonyloxy, a (C2-C10)alkynylcarbonyloxy, an aminocarbonyl, a (C1-C10)alkylcarbonylamino, a (C2-C10)alkenylcarbonylamino, a (C2-C10)alkynylcarbonylamino, a (C3-C7)cycloalkyl, a thio(C1-C10)alkyl, a thio(C2-C10)alkenyl, a thio(C2-C10)alkynyl, a (C1-C10)alkylsilyl, a (C2-C10)alkenylsilyl, a (C2-C10)alkynylsilyl, a (C6-C20)arylsilyl, a (C3-C20)heteroaryl, a 5- to 7-membered heterocycloalkyl, or —NR$^{21}$R$^{22}$, wherein R$^{21}$ and R$^{22}$ are each independently a (C1-C10)alkyl, a (C2-C10)alkenyl, a (C2-C10)alkynyl, a (C6-C20)aryl, a di(C1-C10)alkylamino, a di(C2-C10)alkenylamino, or a di(C2-C10)alkynylamino;

$R^{55}$ and $R^{56}$ are each independently a (C6-C20) aryl, a (C6-C20)ar(C1-C10)alkyl, a (C6-C20)ar(C2-C10)alkenyl, a (C6-C20)ar(C2-C10)alkynyl, a (C1-C10)alkyl, a (C2-C10)alkenyl, a (C2-C10)alkynyl, a (C3-C7)cycloalkyl, a (C3-C20)heteroaryl, a 5- to 7-membered heterocycloalkyl, a (C1-C10)alkoxy, a (C6-C20)aryloxy, a (C1-C10)alkoxycarbonyl, a (C1-C10)alkylcarbonyloxy, a (C2-C10)alkenylcarbonyloxy, a (C2-C10)alkynylcarbonyloxy, an aminocarbonyl, a (C1-C10)alkylcarbonylamino, a (C2-C10)alkenylcarbonylamino, a (C2-C10)alkynylcarbonylamino, a di(C1-C10)alkylamino, a di(C2-C10)alkenylamino, a di(C2-C10)alkynylamino, a (C1-C10)alkylsilyl, a (C2-C10)alkenylsilyl, a (C2-C10)alkynylsilyl, or a (C6-C20)arylsilyl, or $R^{45}$ and $R^{46}$ may be taken together via a (C3-C10)alkylene or a (C3-C10)alkenylene to form a ring;

the aryl, the aralkyl, the aralkenyl, the aralkynyl, the alkyl, the alkenyl, the alkoxy, the aryloxy, the alkoxycarbonyl, the alkylcarbonyloxy, the alkenylcarbonyloxy, the alkynylcarbonyloxy, the cycloalkyl, the heteroaryl, or the heterocycloalkyl of $R^{51}$ to $R^{54}$, and the aryl, the aralkyl, the aralkenyl, the aralkynyl, the alkyl, the alkenyl, the cycloalkyl, the heteroaryl, the heterocycloalkyl, the alkoxy, the aryloxy, the alkoxycarbonyl, the alkylcarbonyloxy, the alkenylcarbonyloxy, the alkynylcarbonyloxy, the aminocarbonyl, the alkylcarbonylamino, the alkenylcarbonylamino, the alkynylcarbonylamino, the dialkylamino, the dialkenylamino, the dialkynylamino, the alkylsilyl, the alkenylsilyl, the alkynylsilyl, or the arylsilyl of $R^{55}$ and $R^{56}$ may be further substituted with one or more selected from a (C1-C10)alkyl, a (C2-C10)alkenyl, a (C2-C10)alkynyl, a (C1-C10)alkoxy, a (C6-C20)aryloxy, a di(C1-C10)alkylamino, a di(C2-C10)alkenylamino, a di(C2-C10)alkynylamino, and a halogen;

X is a halogen; and a is an integer of 0 or ranging from 1 to 3, b and c are each independently an integer of 1 or 2).

Preferably, the oligomerization catalyst may be compound in which $R^{46}$ to $R^{48}$ in Formulas 5 and 6 are each independently hydrogen, a (C1-C10)alkyl, or a halo(C1-C10)alkyl; $R^{51}$ to $R^{54}$ are each independently a (C6-C20) aryl; $R^{55}$ and $R^{56}$ may be each independently a (C1-C10) alkyl, or a compound in which $R^{51}$ to $R^{54}$ are each independently a (C6-C20) aryl; and $R^{55}$ and $R^{56}$ are each independently a (C1-C10)alkyl, and a is 0.

Hereinafter, preferred examples and comparative examples of the present invention will be described. However, it should be understood that the following examples are merely preferred examples of the present invention, and are not intended to limit the present invention.

Preparation Example

As a catalyst for ethylene oligomerization, bis-[(S,S)-(phenyl)$_2$PCH(methyl)CH(methyl)P(phenyl) 2dichloride (µ-chloride)chromium] (5.3 µmol-Cr) was prepared according to the following method.

2.1 mg (5.3 umol) of chromium(III) trichloride tetrahydrofuran (CrCl$_3$(THF)$_3$) was dissolved in 1 mL of methane dichloride, and a solution obtained by dissolving 2.4 mg (5.6 umol) of an (S,S)-(phenyl)$_2$PCH(methyl)CH(methyl)P(phenyl)$_2$ ligand compound in 1 mL of methane dichloride was slowly added to the resulting solution, and reacted for 60 minutes. Thereafter, the resulting mixture was further stirred for 5 minutes, and 1.3 mg (5.6 umol) of sodium hexafluoroacetylacetonate was then slowly added to the mixture. Then, the reaction product was further stirred for 3 hours, and then filtered using a 0.2 um syringe filter. The resulting filtrate was dried under vacuum to remove volatile matters, thereby obtaining dried dark green solids, which were then used as the oligomerization catalysts of Examples and Comparative Examples as will be described below.

This catalyst is a catalyst having very excellent ethylene oligomerization reaction activity and selectivity, and may be identified more clearly with reference to Korean Patent Application No. 10-2016-0065709.

Example 1

A 2,000 mL stainless steel pressure reactor was washed with nitrogen under vacuum, and 1 L of methylcyclohexane (MCH) was put into the reactor. Modified methylaluminoxane (m-MAO3A, Akzo Nobel, 18% by weight in heptane) (1.57 g) as a cocatalyst, and 2.0 mL (4 mmol) of a 2.0

M trimethylaluminum heptane solution were sequentially put into the reactor, and a temperature of the reactor was then increased to 60° C. Thereafter, 3.1 mg of bis-[(S,S)-(phenyl)$_2$PCH(methyl)CH(methyl)P(phenyl)$_2$dichloride(µ-chloride)chromium] (5.3 µmol-Cr) prepared in Preparation Example was put into the reactor, and the reactor was filled with ethylene until the pressure in the reactor reached 20 bar. Then, ethylene was continuously fed to the reactor while maintaining the pressure in the reactor, and an oligomerization reaction was performed while stirring at 250 rpm for 2 hours. Subsequently, the stirring was stopped, and the temperature of the reactor was cooled to 10° C.

Next, a solution obtained by diluting 1.5 g of PPG1000 (Sigma-Aldrich, Polypropylene glycol having a number average molecular weight of 1,000 and 51 carbon atoms) as a catalyst deactivator in 100 mL of methylcyclohexane (MCH) was added to the solution obtained as a result of the oligomerization reaction to stop the reaction. Thereafter, the reaction product was filtered and separated. Then, 20 mL of the resulting filtrate was dried at 100° C. for an hour in a separate flask, and then subjected to GC-FID analysis using heptane as the internal standard, and the purity of 1-octene was confirmed. The results are summarized in the following Table 2. The amount (based on the number of moles) of the introduced catalyst deactivator was 5 times higher than the total number of moles of aluminum in the cocatalyst.

Then, a process of separating a catalyst deactivator was simulated using ASPEN PLUS V8.8 (AspenTech) to evaluate the separation efficiency between the produced linear alpha olefins (LAOs) and the catalyst deactivator. Assuming that up to C20 components were also used as the product, components of the mixture flowing in a distillation column configured to separate C10 or more components were set as listed in the following Table 1. When it was assumed that the number of the distillation column stages was set to 10, and a temperature in a condenser was set to 194° C., a heat duty (kcal/hr) of the condenser required to separate the catalyst deactivator in the mixture to a level of 0.1% by weight, a heat duty (kcal/hr) required for a reheater, and a recycling ratio were calculated. The results are summarized in Table 2.

Example 2

The purity of 1-octene in the reaction product was determined in the same manner as in Example 1, except that PPG2000 (Sigma-Aldrich, Polypropylene glycol having a number average molecular weight of 2,000 and 102 carbon atoms) was used as the catalyst deactivator after the oligomerization reaction. Thereafter, the separation efficiency of the catalyst deactivator was evaluated. The results are summarized in Table 2.

Example 3

The purity of 1-octene in the reaction product was determined in the same manner as in Example 1, except that PPG725 (Sigma-Aldrich, Polypropylene glycol having a number average molecular weight of 725 and 36 carbon atoms) was used as the catalyst deactivator after the oligomerization reaction. Thereafter, the separation efficiency of the catalyst deactivator was evaluated. The results are summarized in Table 2.

Example 4

The purity of 1-octene in the reaction product was determined in the same manner as in Example 1, except that PPG425 (Sigma-Aldrich, Polypropylene glycol having a number average molecular weight of 425 and 21 carbon atoms) was used as the catalyst deactivator after the oligomerization reaction. Thereafter, the separation efficiency of the catalyst deactivator was evaluated. The results are summarized in Table 2.

Comparative Example 1

The purity of 1-octene in the reaction product was determined in the same manner as in Example 1, except that 2-ethyl-1-hexanol (Sigma-Aldrich) was used as the catalyst deactivator after the oligomerization reaction. Thereafter, the separation efficiency of the catalyst deactivator was evaluated. The results are summarized in Table 2. Because the boiling point of 2-ethylhexanol was distributed between the components to be separated, two distillation columns were used, and the number of each of the two distillation columns' stages were set to 40 and 30.

Comparative Example 2

The purity of 1-octene in the reaction product was determined in the same manner as in Example 1, except that 1-pentanol (Sigma-Aldrich) was used as the catalyst deactivator after the oligomerization reaction. Thereafter, the separation efficiency of the catalyst deactivator was evaluated. The results are summarized in Table 2.

TABLE 1

| | Inflow rate (kg/hr) | | | | | |
|---|---|---|---|---|---|---|
| | Example 1 | Example 2 | Example 3 | Example 4 | Comparative Example 1 | Comparative Example 2 |
| C10 alpha olefin | 1,200 | 1,200 | 1,200 | 1,200 | 1,200 | 1,200 |
| C12 alpha olefin | 800 | 800 | 800 | 800 | 800 | 800 |
| C14 alpha olefin | 550 | 550 | 550 | 550 | 550 | 550 |
| C16 alpha olefin | 300 | 300 | 300 | 300 | 300 | 300 |
| C18 alpha olefin | 200 | 200 | 200 | 200 | 200 | 200 |
| C20 alpha olefin | 120 | 120 | 120 | 120 | 120 | 120 |
| Catalyst deactivator | 600 | 600 | 600 | 600 | 600 | 600 |

TABLE 2

|  |  | Example 1 | Example 2 | Example 3 | Example 4 | Comparative Example 1 | Comparative Example 2 |
|---|---|---|---|---|---|---|---|
|  | Purity (%) of 1-octene oligomerization reaction product | 98.95 | 98.94 | 98.88 | 98.91 | 98.90 | 98.79 |
| Evaluation of separation efficiency of catalyst deactivator | Condenser heat duty (kcal/hr) | −326,000 | −326,000 | −364,000 | −367,000 | −5,831,000 | −584,000 |
|  | Recycling ratio | 0.091 | 0.090 | 0.215 | 0.220 | 12.101, 6.808 | 7.55 |
|  | Reheater heat duty (kcal/hr) | 786,000 | 654,000 | 786,000 | 796,000 | 2,053,000 | 910,000 |

From Table 2, it can be seen that the purity of 1-octene in the oligomerization reaction product was very high in all Examples 1 to 4.

Also, it can be seen that the heat duties required for the condenser and the reheater in Comparative Examples 1 and 2 were very higher than those of Examples, and a high level of the recycling ratio of the mixture to be separated was required when the catalyst deactivator and the linear alpha olefins having 20 or more carbon atoms were separated by distillation. Accordingly, increases in the process energy and process time required to separate the catalyst deactivator from the product were inevitable in the case of Comparative Examples, which resulted in severely degraded economic feasibility of a process and highly lowered actual industrial applicability.

Further, it can be seen that the catalyst deactivators of Examples 1 and 2 having a number average molecular weight of 1,000 or more had relatively superior separation efficiency, compared to those of Examples 3 and 4.

Accordingly, it was confirmed that the catalyst deactivator of the present invention had very excellent separation efficiency from the oligomerization reaction product, compared to those of Comparative Examples. From these results, the catalyst deactivator of the present invention is expected to remarkably reduce processing costs because the present invention may achieve a high added value of an ethylene oligomerization reaction, and is applicable to actual industries.

The invention claimed is:

1. A method for oligomerizing olefins, the method comprising:
   introducing an oligomerization transition metal catalyst, an olefin monomer, and a solvent into a reactor and performing an olefin oligomerization reaction to produce oligomers;
   introducing a catalyst deactivator to a reaction product of the oligomerization reaction to deactivate the catalyst, wherein the catalyst deactivator includes one or more functional groups containing at least one selected from the group consisting of oxygen, phosphor, nitrogen, and sulfur, and has a number average molecular weight of 400 or more;
   separating the oligomers by distillation in a distiller; and
   separating the catalyst deactivator through the bottom end of the distiller,
   wherein the catalyst deactivator is a phosphine-based compound, an amine-based compound, a thiol-based compound, an ether-based compound, an ester-based compound, carboxylic acid, or a ketone-based compound,
   wherein the transition metal catalyst is represented by $ML^1(L^2)_p(X)_q$ or $M_2X^1{}_2L^1{}_2(L^2)_y(X)_z$, wherein M is a transition metal, $L^1$ is a heteroligand, $L^2$ is an organic ligand, X and $X^1$ are each independently a halogen, p is an integer of 0 or 1 or more, q is an integer of (oxidation number of M−p), y is an integer of 2 or more, and z is an integer of (2× oxidation number of M) −y,
   wherein the heteroligand $L^1$ has a P—C—C—P backbone structure represented by the following Formula 3, or a P—N—P backbone structure represented by the following Formula 4,

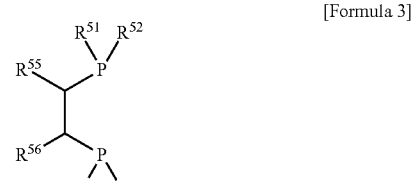

[Formula 3]

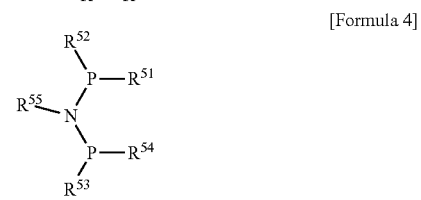

[Formula 4]

wherein $R^{51}$ to $R^{54}$ are each independently a hydrocarbyl, a substituted hydrocarbyl, a heterohydrocarbyl, or a substituted heterohydrocarbyl, and wherein $R^{55}$ and $R^{56}$ are each independently a hydrocarbyl or a substituted hydrocarbyl, or $R^{55}$ and $R^{56}$ may be taken together via hydrocarbylene, substituted hydrocarbylene, heterohydrocarbylene, or substituted heterohydrocarbylene to form a ring.

2. The method of claim 1, wherein the number average molecular weight of the catalyst deactivator is greater than or equal to 600.

3. The method of claim 1, wherein the catalyst deactivator has 31 or more carbon atoms based on the number average molecular weight thereof.

4. The method of claim 1, wherein the catalyst deactivator is represented by the following Formula 1:

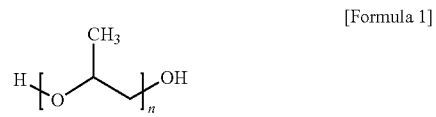

[Formula 1]

(wherein n ranges from 11 to 170).

5. The method of claim 1, wherein 1-octene is included at 30% by weight or more, based on 100% by weight of linear alpha olefins in the reaction product of the oligomerization reaction.

6. The method of claim 1, wherein the cocatalyst is further introduced when the oligomerization transition metal catalyst, the olefin monomer, and the solvent are introduced into the reactor to perform the olefin oligomerization reaction, and the cocatalyst is an aluminum compound, an organoaluminoxane, an organoboron compound, or a mixture thereof.

7. The method of claim 6, wherein an amount of the introduced catalyst deactivator is in a range of 1.5 to 20 times higher than the total number of moles of aluminum, boron, or a combination thereof in the cocatalyst based on the number of moles.

8. The method of claim 1, wherein, in the separating of the oligomers, the oligomers are separated into C5 or less oligomers; 1-hexene; C6 other than the 1-hexene, and C7 oligomers; 1-octene; and C8 other than the 1-octene, and C9-C20 oligomers.

9. The method of claim 1, wherein the olefin monomer is ethylene, and the oligomers include a mixture of C4-C40 linear alpha olefins.

10. A method for oligomerizing olefins, the method comprising:
introducing an oligomerization transition metal catalyst, an olefin monomer, and a solvent into a reactor and performing an olefin oligomerization reaction to produce oligomers;
introducing a catalyst deactivator to a reaction product of the oligomerization reaction to deactivate the catalyst, wherein the catalyst deactivator includes oxygen, and has a number average molecular weight of 1,000 to 10,000;
separating the oligomers by distillation through the top or middle portion of a distiller; and
separating the catalyst deactivator through the bottom end of the distiller, wherein the catalyst deactivator is represented by the following Formula 1:

[Formula 1]

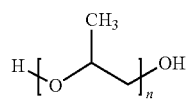

wherein the transition metal catalyst is represented by $ML^1(L^2)_p(X)_q$ or $M_2X^1_2L^1_2(L^2)_y(X)_z$, wherein M is a transition metal, $L^1$ is a heteroligand, $L^2$ is an organic ligand, X and $X^1$ are each independently a halogen, p is an integer of 0 or 1 or more, q is an integer of (oxidation number of M–p), y is an integer of 2 or more, and z is an integer of (2× oxidation number of M) –y, wherein the heteroligand $L^1$ has a P—C—C—P backbone structure represented by the following Formula 3,

[Formula 3]

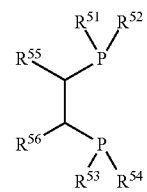

wherein $R^{51}$ to $R^{54}$ are each independently a hydrocarbyl, a substituted hydrocarbyl, a heterohydrocarbyl, or a substituted heterohydrocarbyl, and wherein $R^{55}$ and $R^{56}$ are each independently a hydrocarbyl or a substituted hydrocarbyl, or $R^{55}$ and $R^{56}$ may be taken together via hydrocarbylene, substituted hydrocarbylene, heterohydrocarbylene, or substituted heterohydrocarbylene to form a ring.

* * * * *